US011819586B2

(12) United States Patent
Grinstead et al.

(10) Patent No.: US 11,819,586 B2
(45) Date of Patent: *Nov. 21, 2023

(54) FOGGING SYSTEM AND METHODS FOR ENCLOSED CHAMBERS

(71) Applicant: GCMG COMPANIES, LLC, Oviedo, FL (US)

(72) Inventors: Steven T. Grinstead, Oviedo, FL (US); Corwin A Warner, Leesburg, VA (US)

(73) Assignee: GCMG COMPANIES, LLC, Oviedo, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/657,804

(22) Filed: Apr. 4, 2022

(65) Prior Publication Data

US 2022/0226524 A1 Jul. 21, 2022

Related U.S. Application Data

(63) Continuation of application No. 16/991,180, filed on Aug. 12, 2020, now Pat. No. 11,291,740.

(Continued)

(51) Int. Cl.
*A61L 2/22* (2006.01)
*A61L 9/14* (2006.01)

(52) U.S. Cl.
CPC .. *A61L 2/22* (2013.01); *A61L 9/14* (2013.01)

(58) Field of Classification Search
CPC ... A61L 2/18; A61L 2/186; A61L 2/20; A61L 2/208; A61L 2/22; A61L 9/14
See application file for complete search history.

(56) References Cited

U.S. PATENT DOCUMENTS 5,906,794 A 5/1999 Childers
7,186,373 B2 3/2007 Centanni
(Continued)

FOREIGN PATENT DOCUMENTS

EP 1378250 B1 1/2004
KR 100913632 8/2009

OTHER PUBLICATIONS

Steris "VHP® X10 Biodecontamination Unit" https://www.sterislifesciences.com/~/media/files/lifesciences_com/pdf/equipment/lsepss4056aenevhp%20x10%20biodecontamination%20unit32014.ashx; pp. 2, ** See U.S. Appl. No. 16/991,180.

(Continued)

*Primary Examiner* — Timothy C Cleveland
(74) *Attorney, Agent, or Firm* — Allen, Dyer, Doppelt + Gilchrist, PA

(57) ABSTRACT

A system for disinfecting an enclosed chamber may include a housing, an inlet and an outlet carried by the housing to be connected in an airflow path with the enclosed chamber, a dehumidification chamber carried by the housing, and a blower carried by the housing and connected to the airflow path between the inlet and outlet and configured to circulate air through the airflow path. The system may further include an atomizing nozzle connected to a disinfectant fluid reservoir and an air compressor and configured to atomize disinfectant within the airflow path during a treatment phase, an airflow valve connected in the airflow path between the inlet and dehumidification chamber, and a controller configured to operate the airflow valve to connect the dehumidification chamber into the airflow path during an evacuation phase and disconnect the dehumidification from the airflow path during the treatment phase.

20 Claims, 9 Drawing Sheets

Related U.S. Application Data

(60) Provisional application No. 62/885,414, filed on Aug. 12, 2019.

(56) References Cited

U.S. PATENT DOCUMENTS

| | | | |
|---|---|---|---|
| 7,550,122 | B2 | 6/2009 | Buczynski et al. |
| 7,640,782 | B2 | 1/2010 | Hill |
| 8,071,021 | B2 | 12/2011 | Hill |
| 8,529,832 | B2 | 9/2013 | Lee |
| 9,480,764 | B2 | 11/2016 | Tremblay et al. |
| 9,717,810 | B2 | 8/2017 | Grinstead |
| 10,092,668 | B2 | 10/2018 | Grinstead |
| 11,291,740 | B2 * | 4/2022 | Grinstead .............. A61L 9/14 |
| 2013/0078153 | A1 | 3/2013 | Hill et al. |
| 2018/0353631 | A1 | 12/2018 | Grinstead et al. |
| 2019/0167829 | A1 | 6/2019 | Grinstead |

OTHER PUBLICATIONS

Steris "VHP® X10 Biodecontamination Unit" https://shop.steris.com/en/us/enclosed-space-biodecontamination/vhp-x10-biodecontamination-unit?fetchFacets=true#facet:&productBeginIndex:0&facetLimit:&orderBy:&pageView:EPP&minPrice:&maxPrice:&pageSize:& pp. 3, ** See U.S. Appl. No. 16/991,180.

ISO Tech Desing "Integrated H2O2 Generator" https://www.isotechdesign.com/ product/pharmaceuticals/integrated-h2o2-generator/ pgs/ 7 retreived from internet Feb. 7, 2022, ** See U.S. Appl. No. 16/991,180.

Steris "VHP® X10 Biodecontamination Unit" https://partcatalog.steris.com/InService/delivery/?usertype=ecomm#/V=2/topic/Topic::Vj0xfnsicklkljoiVkhQLUVOQ19JU19WSFAtRU5DLVgxMCIsIm9wljpbIIZIUC1FTkNfSVNfVkhQLUVOQy1YMTAiLCJJU19WSFAtRU5DLVgxMC5JUEliXSwibm4iOjEyLCJ0cyI6MTYzMzU1MzkzMTkwN30?filterId=ProductInstance::Vj0xfnsicklkljoiUk9PVCBQUk9EVUNUIiwib3AiOlsiUk9PVCBQUk9EVUNUIiwiVkhQliwiVkhQLUVOQyIsIIZIUC1FTkMtWDEwIiwiUElfVkhQLUVOQy1YMTBfNzY0MzI3MzgyLTAxII0sIm5uIjotMSwidHMiOjE2MzM1NTM4OTY2OTR9&pfilter=76432738201%20%255BVHP%25C2%25AE%20X10%20Biodecontamination%20Unit%255D; pp. 6;retreived from internet Jan. 31, 2022, ***** See U.S. Appl. No. 16/991,180.

* cited by examiner

```
                    ┌─────────┐
                    │  START  │──91
                    └─────────┘
                         │
                         ▼
         ┌──────► ╱ TREATMENT ╲ ──92
    NO ──┤        ╲ PHASE START? ╱
         │              │
         │             YES
         │              ▼
         │    ┌──────────────────────────────┐
         │    │ OPERATE COMPRESSOR           │
         │    │ (CONTINUOUS/NONCONTINUOUS) TO│──93
         │    │ INTRODUCE ATOMIZED DISINFECTANT│
         │    │ INTO AIRFLOW PATH WITH ATOMIZING│
         │    │ NOZZLE IN EVAPORATION CHAMBER │
         │    └──────────────────────────────┘
         │              │
         │              ▼
    NO ──┤        ╱ TREATMENT  ╲ ──94
         │        ╲ PHASE COMPLETE? ╱
                        │
                       YES
                        ▼
              ┌──────────────────────┐
              │ CEASE OPERATING COMPRESSOR │──95
              └──────────────────────┘
                        │
         ┌──────────────┤
         │              ▼
         │    ┌──────────────────────────────┐
         │    │ OPERATE AIRFLOW VALVE TO DIVERT│
         │    │ AIRFLOW PATH THROUGH DESICCATION│──96
         │    │ CHAMBER TO REMOVE ATOMIZED    │
         │    │ DISINFECTANT FROM AIRFLOW PATH│
         │    └──────────────────────────────┘
         │              │
         │              ▼
    NO ──┤        ╱ EVACUATION ╲ ──97
                  ╲ PHASE COMPLETE? ╱
                        │
                       YES
                        ▼
                  ┌─────────┐
                  │ FINISH  │──98
                  └─────────┘
```

*FIG. 9*

FOGGING SYSTEM AND METHODS FOR ENCLOSED CHAMBERS

CROSS-REFERENCE TO RELATED APPLICATIONS

This application is a continuation of U.S. application Ser. No. 16/991,180 filed Aug. 12, 2020, which claims the benefit of U.S. Provisional App. No. 62/885,414 filed Aug. 12, 2019, which are hereby incorporated herein in their entireties by reference.

TECHNICAL FIELD

The present invention relates to the field of disinfecting, deodorizing, preserving, or sterilizing, and, more particularly, to apparatuses and methods for delivery of disinfecting, deodorizing, preserving, or sterilizing solutions.

BACKGROUND

Risk factors associated with pathogen exposure from chambers and enclosures designed to be germ free are well known. Therefore, biological decontamination equipment is used to maintain the safety of these enclosures. Traditionally, specialized service providers are required to operate such equipment due to the inherent hazards in exposure to high concentrations of chemical sterilant in vapor or gaseous form.

For example, one approach that is used for sterilization purposes for such enclosures or other closed loop decontamination applications is decontamination by hydrogen peroxide (DHP). More particularly, a high concentration aqueous hydrogen peroxide solution (typically 50% or more by weight of $H_2O_2$) is evaporated, brought into contact with a hot gas stream and fed into the enclosure to be sterilized. This process is often called "gassing". Afterwards, the enclosure is purged with air until the hydrogen peroxide level is at an approved safety level (e.g., 1 part per million by volume).

Nevertheless, such DHP delivery systems may pose safety risks not only in terms of the high concentrations of hydrogen peroxide used, but also as a result of the heating process. That is, typical approaches which rely on delivering high concentrations of $H_2O_2$ (or $ClO_2$) gas to enclosed spaces heat the gas so that it does not reach dew point levels. This is because concentrations of these solutions increase substantially on surfaces in which it condenses, causing significant material compatibility concerns and also concerns over accidental exposure to people from leaking chambers.

SUMMARY

A system for disinfecting an enclosed chamber may include a housing, an inlet and an outlet carried by the housing to be connected in an airflow path with the enclosed chamber, a dehumidification chamber carried by the housing, and a blower carried by the housing and connected to the airflow path between the inlet and outlet and configured to circulate air through the airflow path. The system may further include an atomizing nozzle connected to a disinfectant fluid reservoir and an air compressor and configured to atomize disinfectant within the airflow path during a treatment phase, an airflow valve connected in the airflow path between the inlet and dehumidification chamber, and a controller configured to operate the airflow valve to connect the dehumidification chamber into the airflow path during an evacuation phase and disconnect the dehumidification from the airflow path during the treatment phase.

In an example embodiment, the system may also include a neutralizing fluid reservoir carried by the housing and a fluid valve connecting the neutralizing fluid reservoir to the airflow path between the inlet and outlet, and the controller may be further configured to, during a neutralization phase, operate the fluid value to introduce neutralizing fluid into the airflow path. In some embodiments, the controller may be configured operate the air compressor continuously during a first portion of the treatment phase, and non-continuously during a second portion of the treatment phase.

By way of example, the dehumidification chamber may comprise a desiccation chamber configured to receive a desiccation cartridge. In an example embodiment, the system may also include a humidity sensor connected in the airflow path between the inlet and outlet and to the controller, and the controller may be configured to operate the compressor during the treatment phase responsive to the humidity sensor. The humidity sensor may comprise a hydrogen peroxide sensor, for example.

In an example implementation, the blower may be upstream from the atomizing nozzle in the airflow path. Furthermore, the controller may be further configured to operate the blower non-continuously during the treatment phase. In some embodiments, an external disinfectant fluid port may be carried by the housing to be connected to the disinfectant fluid reservoir, and an external air compressor port may be carried by the housing to be connected to the air compressor.

A related method for disinfecting an enclosed chamber may include connecting an inlet and an outlet of a fogging injection station in a closed airflow path with the enclosed chamber. The fogging injection station may include a housing, a dehumidification chamber carried by the housing, a blower carried by the housing and connected to the airflow path between the inlet and outlet and configured to circulate air through the airflow path, an atomizing nozzle connected to a disinfectant fluid reservoir and an air compressor and configured to atomize disinfectant within the airflow path during a treatment phase, an airflow valve connected in the airflow path between the inlet and dehumidification chamber, and a controller. The method may further include, during an evacuation phase, using the controller to operate the airflow valve to connect the dehumidification chamber into the airflow path, and during the treatment phase, using the controller to operate the airflow valve to disconnect the dehumidification chamber from the airflow path.

BRIEF DESCRIPTION OF THE DRAWINGS

FIG. 9 is a flow diagram illustrating method aspects associated with the systems of FIGS. 1 and 8.

DETAILED DESCRIPTION

The present disclosure is provided with reference to the accompanying drawings, in which various embodiments are shown. However, other embodiments in many different forms may be used, and the disclosure should not be construed as limited to the particular embodiments set forth herein. Rather, these embodiments are provided so that this disclosure will be thorough and complete, and will fully convey the claim scope to those skilled in the art. Like numbers refer to like elements throughout, and prime notation is used to indicate similar elements in different embodiments.

Figure 1:
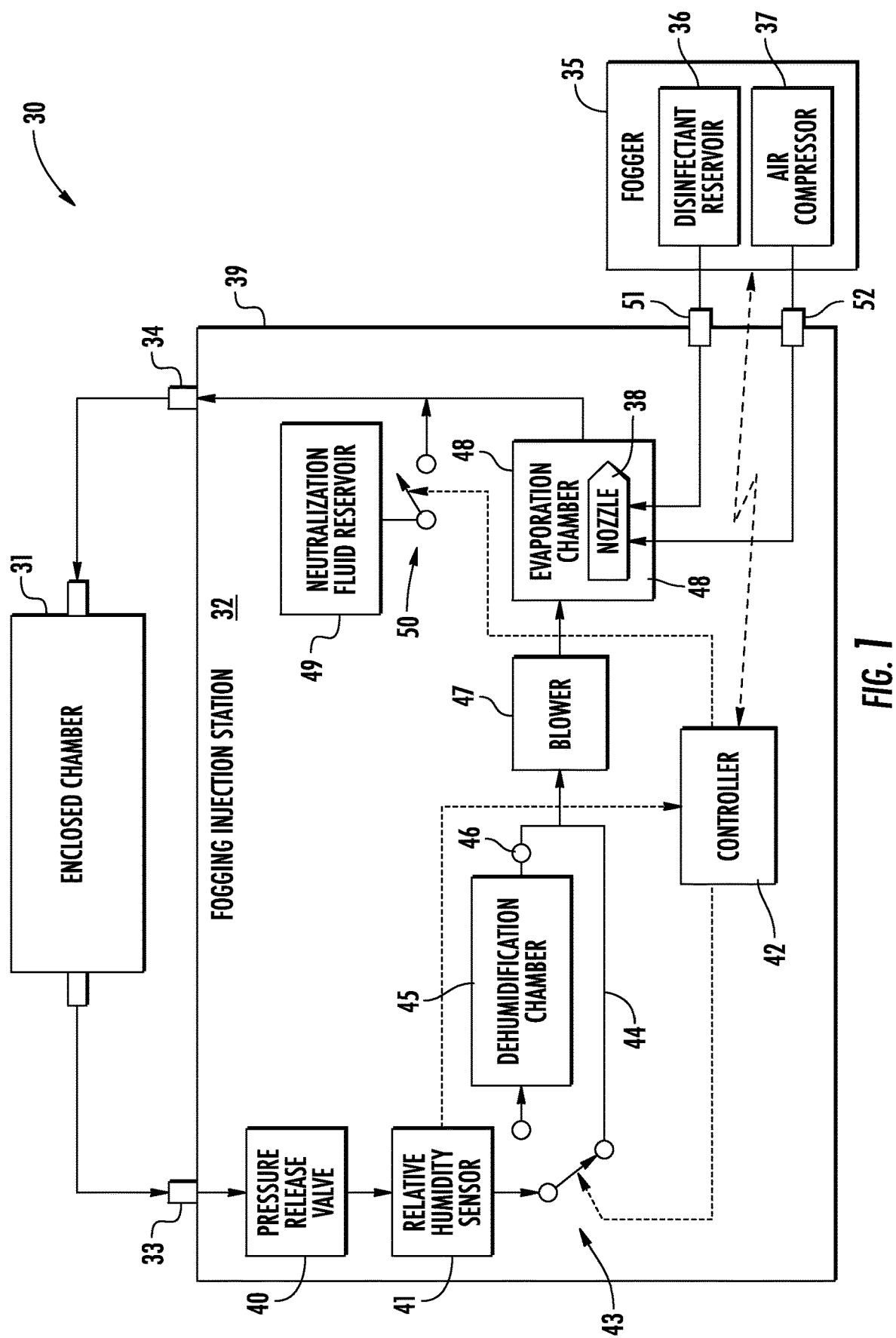
FIG. 1 is a schematic block diagram of a system for disinfecting an enclosed chamber in accordance with an example embodiment.
Figure 2:
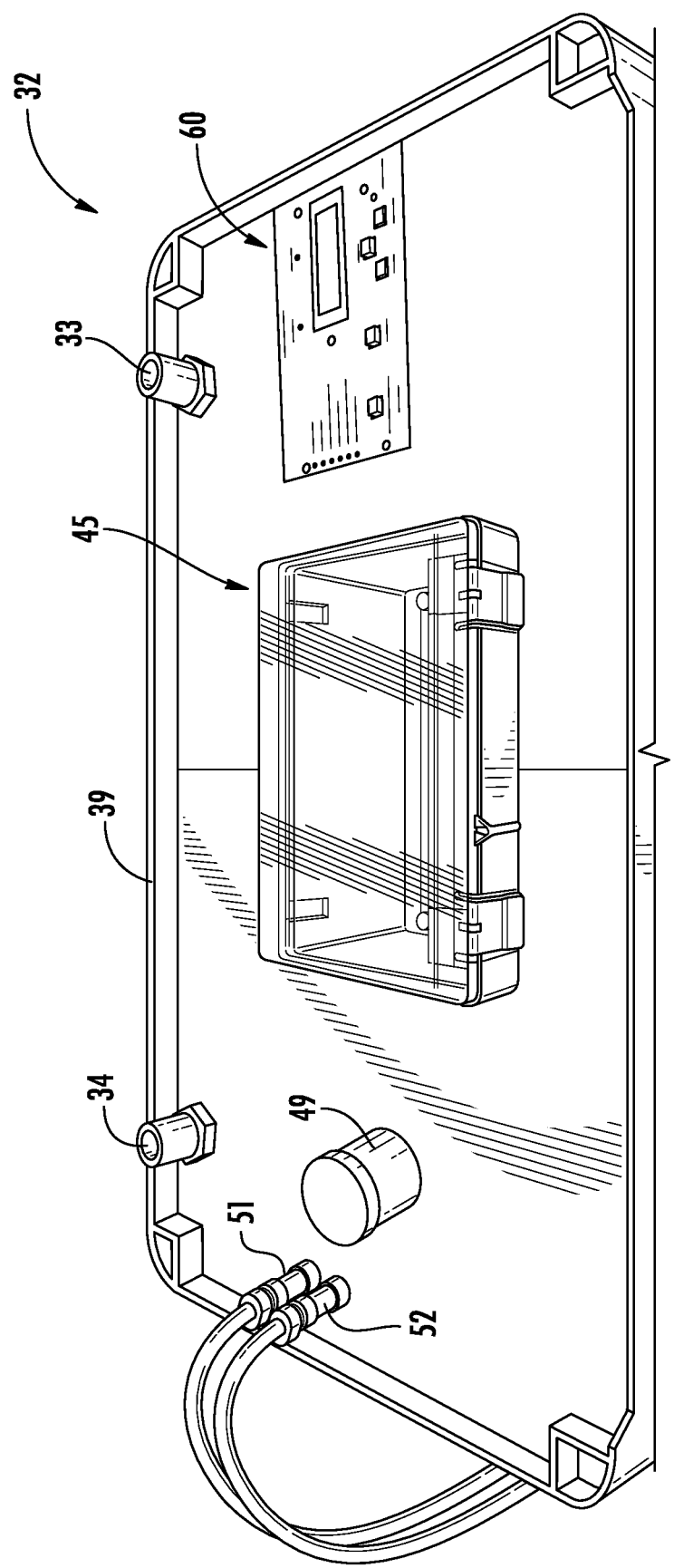
FIG. 2 is a perspective view of an example fogging injection station which may be used in the system of FIG. 1.
Figure 3:
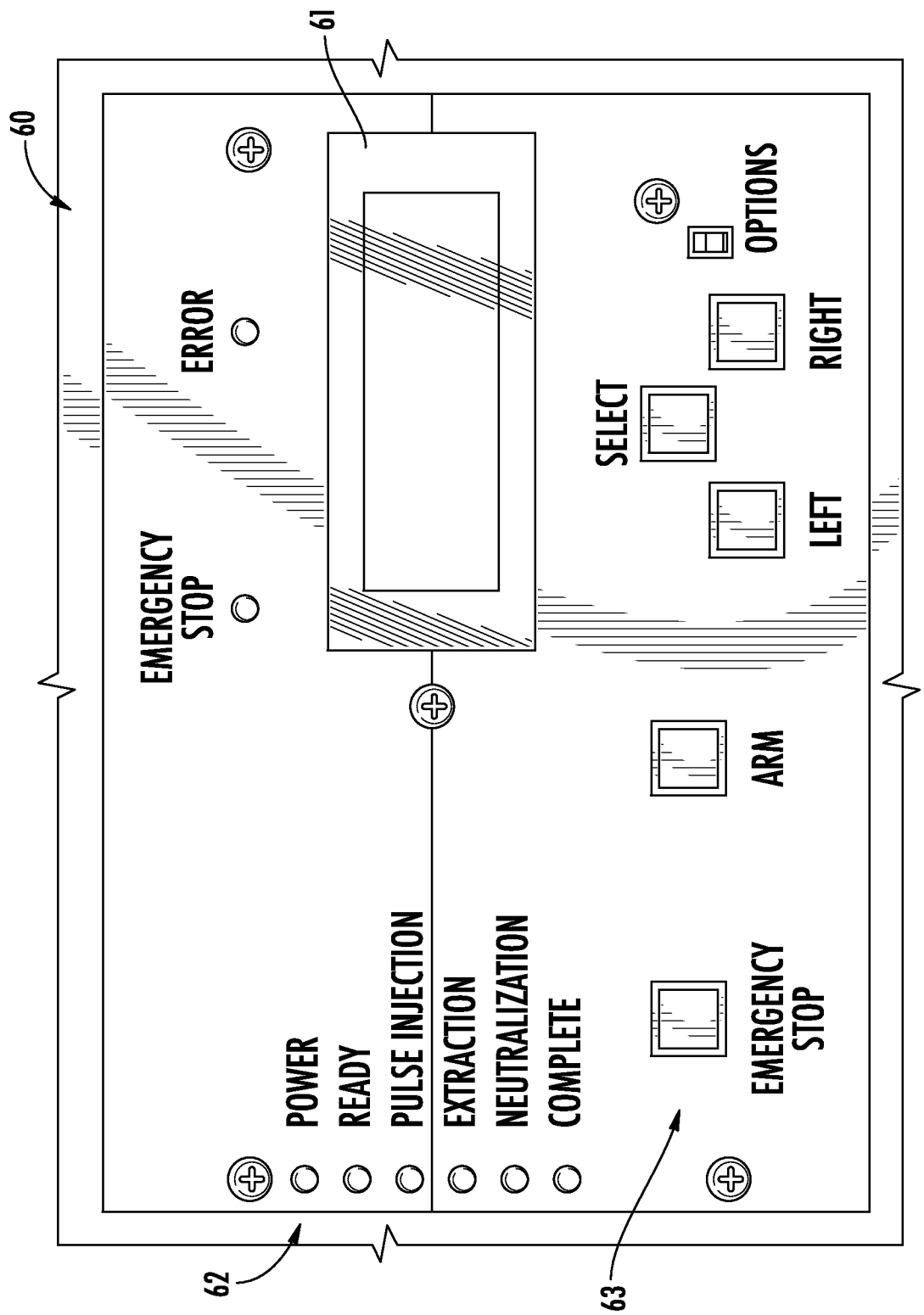
FIG. 3 is a top view of the control panel of the fogging injection station of FIG. 2 shown in greater detail.
Figure 4:
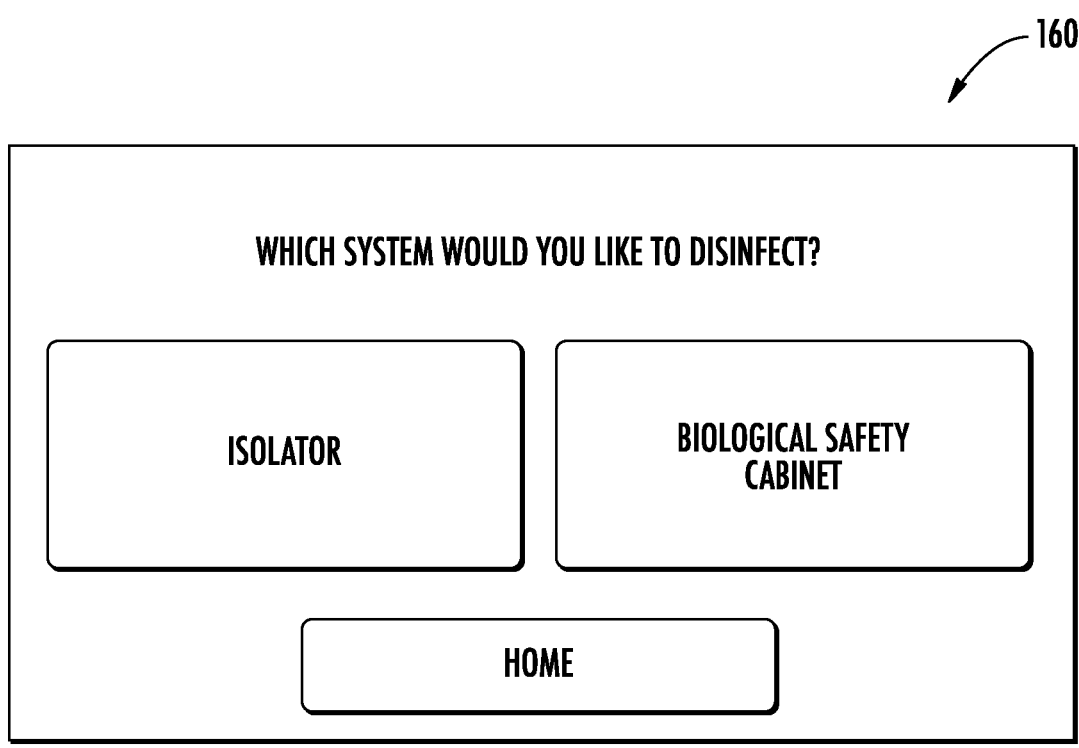
FIGS. 4-7 are display views of a touchscreen control panel which may be used with the fogging injection station of the system of FIG. 1 shown at various operational states of the fogging injection station.

Referring initially to FIGS. 1-3, a system 30 for disinfecting an enclosed chamber or enclosure 31 illustratively includes a fogging injection station 32 which may be used to inject an atomized and/or vaporized fogging fluid into the enclosed chamber for the purpose of disinfecting and/or sterilizing the enclosed chamber. The fogging injection station 32 illustratively includes a housing 39, and an inlet 33 and an outlet 34 carried by the housing which are coupled to the enclosed chamber 31 to be treated. Examples of enclosed chambers 31 which may be treated using the fogging injection station 32 include gnotobiotic chambers, isolators, HEPA filter caissons for clean rooms, air handlers, biological safety cabinets (BSCs), animal transfer stations, hypoxia chambers, mobile laboratories, incubators, etc., and may be used for numerous applications including life sciences, pharmaceuticals, biomedical, and healthcare, for example. The system 30 advantageously provides for decontamination or sterilization of enclosed chambers to prevent human exposure to pathogens or other hazardous materials, as well as to provide disinfected/sterilized enclosures for medical or scientific applications, for example.

In particular, the fogging injection station 32 advantageously introduces an atomized disinfectant solution (e.g., an $H_2O_2$ solution) into the closed airflow path between the fogging injection station and the enclosed chamber 31, which may provide desired efficacy with lower concentrations of $H_2O_2$, for example, and without the need for heated vaporization or boiling of the disinfectant fluid (e.g., at room temperature). That is, the fogging injection station 31 provides for an efficacious application under or over dew point without significant increase to material decomposition or accidental exposure due to lower parts per million concentrations of less than 200 PPM (and more particularly around 170 PPM), as compared to 400-800 or higher with prior approaches which provide a significantly greater risk to operators and those in proximity of the treatment area.

Beginning at the airflow inlet 33 and following the airflow path through the fogging injection station, an optional pressure release valve 40 may be incorporated in the airflow path to prevent the pressure within the airflow path from reaching a level or threshold which may damage components in the airflow path or the enclosed chamber 31. A relative humidity sensor 41 senses or measures the level of humidity in the airflow path, which is provided to and monitored by a controller 42. By way of example, the controller 42 may be implemented using a processor (e.g., microprocessor) and associated memory with non-transitory computer-readable instructions for causing the processor to perform the various operations described herein. Furthermore, a valve (e.g., a T-ball valve) 43 is downstream from the relative humidity sensor and, responsive to the controller 42, is configured to switch the airflow path between a bypass tube 44 and a dehumidification chamber 45. Another valve or de-coupler 46 allows the dehumidification chamber 45, along with the valve 43, to be completely shut off from the air flow path so that the dehumidification chamber may be serviced while the fogging injection station 32 is operational. For example, the dehumidification chamber 46 may be configured to receive a desiccant cartridge or pod, and the valves 43, 46 may be closed to allow a user to replace the desiccant pod as needed for humidity removal. However, in other configurations, the dehumidification chamber 46 may be used for an inline evaporator or dehumidifier, for example. For the present discussion, a desiccation chamber is used.

A blower or fan 47 is downstream from the desiccation chamber 46 and bypass tube 44, and its output blows through an evaporation chamber 48. The output of the evaporation chamber 48 is connected to the airflow outlet 34 of the fogging injection station 32. An optional neutralization fluid reservoir 49 may also be connected into the airflow path between the evaporation chamber 48 and outlet 34 (or directly into the evaporation chamber in some configurations) via a valve 50, which is controlled by the controller 42. It will be appreciated, however, that in different embodiments various components may be located in different positions along the airflow path. Operation of the above-noted components will be described further below.

In the illustrated example, the fogging injection station 32 is coupled to an atomizing fogging device or fogger 35, which includes a disinfectant reservoir 36 for the disinfectant (e.g., a $H_2O_2$ solution, etc.), and an air compressor 37, both of which are in fluid communication with an atomizing nozzle 38 in the fogging injection station which accordingly generates atomized disinfectant in the airflow pathway between the fogging injection station and the enclosed chamber 31. In some embodiments, a priming pump may be used to prime the atomizing nozzle 48 upon startup of the treatment cycle (or later, if appropriate). One particularly advantageously example of such a fogging device 35 is set forth in U.S. Pat. No. 10,092,668 to Grinstead, which is hereby incorporated herein in its entirety by reference.

The fogger 35 also includes its own atomizing nozzle (not shown) and may be used for the treatment of enclosed areas or rooms on its own, but then supply the air compressor 37 and disinfectant reservoir 36 for the fogging injection station 32 when an enclosed chamber 31 is to be treated. In this regard, the fogger 35 and fogging injection station 32 may be used to not only treat enclosed chambers 31, but also the rooms in which the enclosed chambers are present (e.g., as in a laboratory setting). In an example implementation, the housing 39 of the fogging injection station 32 may be a cart with a shelve or rack for the fogger 35, so that the fogger may be housed within and connected with the fogging injection station during treatment of the enclosed chamber 31, and then removed for treatment of the room or storage area where the enclosed chamber is located. Quick connect ports 51, 52 may be used for connecting the disinfectant reservoir 36 and air compressor 37, respectively, to the fogging injection station 32.

Figure 8:
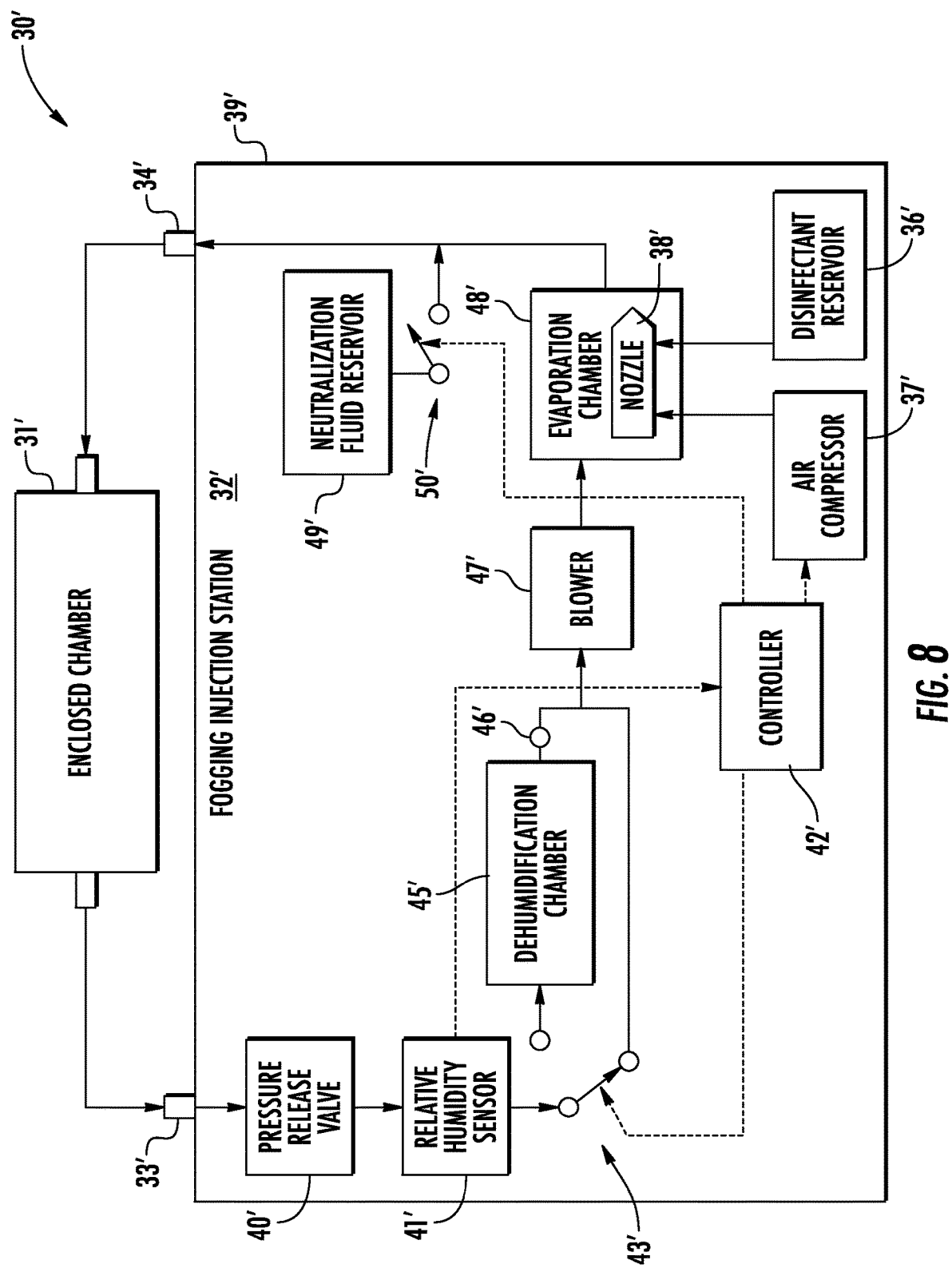
FIG. 8 is a schematic block diagram of an alternative embodiment of the system of FIG. 1.

In an alternative embodiment of the fogging injection station 32' shown in FIG. 8, various components of the atomizing fogging device 35 (e.g., air compressor 37', fluid reservoir 36', etc.) may be included in the fogging injection station itself such that a separate fogging device is not required. That is, the fogging injection station 32' may be considered as an integrated or stand-alone fogging injection station that does not require a separate fogger to be connected thereto.

An example operation flow of the fogging injection station 32 is as follows. Air from the enclosed chamber 31 enters the air inlet 33 of the fogging injection station 32. From there it passes the optional pressure release valve 40 and comes across the relative humidity sensor 41, followed by the valve 43. In the case of a hydrogen peroxide disinfectant, the humidity sensor 41 may be a hydrogen peroxide sensor, or a separate hydrogen peroxide sensor may be included as a secondary type of humidity sensor to measure not only the general humidity in the airflow path, but the $H_2O_2$ in the airflow path as well. However, it should be noted that other types of disinfectants as well as sensors (e.g., temperature sensors, etc.) may be used to provide information to the controller 42 in different embodiments as well. Rigid and/or flex PVC tubing may be used to interconnect the components in the airflow path, and may generally be in a range of 1-3" in diameter (e.g., 2" tubing), although different types of tubing and dimensions may be used in different configurations.

The valve 43 is positioned in the airflow path to allow the airflow to be coupled with the attached fogging device 35 during a treatment phase (via the bypass tube 44 in the illustrated example), and to the dehumidification (e.g., desiccation) chamber 45 during desiccation phase to remove the disinfectant from the enclosure. A solenoid (not shown) may be provided to work in conjunction with the valve 43 for switching between the bypass (disinfecting) and desiccation phases. The controller 42 may be programmed to only allow air flow through the dehumidification chamber 45 during the desiccation phase.

The blower 47 is connected in the flow path and blows air through the evaporation chamber 48 and out through the outlet 34 of the fogging injection station 32 and back into the enclosed chamber 31. As noted above, the dehumidification chamber 45 may be a desiccant chamber for receiving a desiccant or silica gel. In one example, molecular sieve is used as the desiccant, although other suitable desiccants may be used in different embodiments. As noted above, the desiccant may be placed within a removable cartridge or pod, so that new cartridges may be swapped in and out of the chamber 45 as appropriate.

The atomizing nozzle 38 is connected to the disinfectant reservoir 36 and air compressor 37 of the fogger 35 by a pair of side discharge hoses, for example (see FIG. 2). The atomizing nozzle 38 is connected in line to the airflow path within the evaporation chamber 48. That is, the nozzle 38 points in the direction of air flow (downstream toward the outlet 34). When the blower 47 is turned on so that air is passing through it, and the controller 42 instructs the fogger 35 to operate the air compressor 37 (and optionally priming pump), the nozzle 38 sprays atomized disinfectant solution in line in the airflow path. However, in some embodiments the nozzle 38 may be oriented differently.

The atomizing nozzle 38 produces a hybrid aerosolized fogging disinfectant, in that some of the solution will be in a gaseous state (vapor) and some will be in a liquid (droplet) state. For enclosures that have HEPA filters, for example, such filters may prevent passage of the atomized liquid, but the vapor will more readily pass through the HEPA filter. However, the evaporation chamber 48 advantageously helps convert atomized liquid into vapor as well, so that it too may pass into the enclosed chamber 31.

The optional pressure relief valve 40 may also be included in the fogging injection station 32 in the event there is an unexpected rise in pressure. This advantageously helps protect enclosed chambers 31 such as gnotobiotic chambers, for example, that could potentially rupture if the internal pressure is increased too much, and potentially components in the fogging injection station 32 as well. The pressure relief valve 40 may be coupled in the airflow path at other locations prior to the outlet 34 in some embodiments.

In one example implementation, approximately sixteen cubic feet of air is moved through the evaporator per minute (although other amounts of air flow may be provided in different embodiments). If humidity is in a range of 30 to 50%, the vast majority of the humidity will be evaporated into the air flow that goes into the enclosure 31. Accordingly, the fogging injection station 32 is advantageously able to evaporate the suspended liquid droplets in the aerosolized fog injected from the nozzle 38 to advantageously pass through HEPA filters of the enclosed chamber 31.

When the treatment phase is complete, the fogging injection station 32 may then enter an extraction phase when it evacuates the vaporized solution from the enclosed chamber 31. During this phase, the controller 42 causes the solenoid and valve 43 to route the air flow through the desiccation chamber 45, which removes the humidity and, in the case of a hydrogen peroxide-based disinfecting solution, neutralizes and removes it from the treated chamber 31. The type of desiccant and quantity thereof may be selected to provide appropriate extraction for the size of the enclosed chamber 31 being treated and amount of solution that will be introduced into the chamber, as will be appreciated by those skilled in the art. In the example of FIG. 2, a lid on the top of the fogging injection station 32 allows for easy access into the desiccation chamber 45 to replace desiccation pods.

In some embodiments, a neutralization phase may also be provided in which a neutralizing fluid or aqueous solution is introduced into the air flow path from the neutralization fluid reservoir 49 after the extraction phase, such as deionized water, for example. The neutralization solution may advantageously help neutralize any acids remaining on materials and also neutralize ions left behind by the $H_2O_2$ process, which could otherwise degrade materials and/or cause health side effects. In the example of FIG. 2, access to the reservoir 49 is provided on the top of the fogging injection station 32 so that the neutralization solution may be easily refilled. The reservoir 49 may hold on the order of a few ounces of neutralization solution, although larger reservoirs may be used depending on the application. Moreover, in some implementations a pump (not shown) may be associated with the neutralization fluid reservoir 49 and controlled by the controller 42 to pump the neutralization solution into the airflow path during and/or after the evaporation phase. However, other configurations may also be possible (e.g., a gravity fed configuration).

To summarize the operational phases of the fogging injection station 32, as described in the above-noted '668 patent, the initial treatment or killing phase when the disinfectant is being introduced into the enclosed chamber 31 may be divided into two sub-phases, namely a continuous injection to initially bring the chamber up to the desired level (e.g., humidity or $H_2O_2$ level), and then a non-continuously (e.g., intermittent or periodic) injection to maintain the chamber at the desired level (or within a desired range). However, it should be noted that in other embodiments other injection configurations may be used (e.g., just continuous injection, etc.). By way of example, the treatment phase may typically range from thirty minutes to an hour, although other times may be used in different applications.

After the treatment phase, the fogging injection station 32 enters the extraction phase when the disinfectant (e.g., a hydrogen peroxide-based solution) is removed by the desiccant. The desiccation chamber 45 pulls out humidity in liquid form. Moreover, in the case of molecular sieve, for example, it also pulls out gas because it is porous enough to grab the gas molecules as well.

Then, an optional neutralization phase may be provided when the fogging injection station 32 introduces a neutralizing fluid (e.g., deionized water), which brings the humidity up in the enclosure. The hydrogen peroxide is mostly or completely evacuated out of the enclosed chamber 31 being treated by the time of the neutralization phase, which helps to ensure there are no undesired residues or ions within the enclosed chamber as noted above. The fogging injection station 32 may then run a second evaporation phase to lower the humidity in the enclosure (e.g., to remove the deionized water) after the neutralization phase, if desired. Another approach is to just vent or resume normal air flow to the enclosed chamber 31, since at this point it just has air and water (in the case of deionized water as the neutralization fluid) therein.

The controller 42 switches the actuators for the above-noted valves and pumps to connect the spray nozzle, evaporation chamber, desiccation chamber, and neutralization fluid reservoir in the air flow path during the appropriate operational phase. Moreover, in some embodiments, the controller 42 may also control the fogging device 35 (e.g., wirelessly or by a wired connection) to coordinate its operation during the treatment phase, as described further in the above-noted '668 patent. Furthermore, the controller 42 may also be used to control other foggers, e.g., within the same room the fogging injection station is being used in, to coordinate their treatment cycles as well, if desired, as also described further in the '668 patent. The controller 42 may also be configured to change operating parameters during the treatment cycle as appropriate. For example, if it is taking longer for an enclosure 31 to reach the desired humidity or $H_2O_2$ level (as measured by the in-line humidity or $H_2O_2$ sensor) than the baseline programming provides for, the controller 42 may cause the fogging device 35 to extend the continuous injection phase for a longer period of time before switching to the pulse (noncontinuous) injection phase, for example.

More particularly, the various points at which the controller 42 switches between the treatment, evacuation, and neutralization phases may be based upon estimated times for the particular enclosed chamber 31 being treated, which are set through baseline programming. Another option is that switching may occur based upon relative humidity (or $H_2O_2$) levels in the airflow as measured by the relative humidity sensor 41 (and/or $H_2O_2$ sensor). Relative humidity setpoints may be provided as part of the baseline programming by the manufacturer, or in some embodiments an interface may be provided so that a user may adjust these values based upon the particular type of enclosed chamber 31 being treated, the environment in which the treatment is occurring, etc. In some embodiments, a combination of set times and set humidity levels may be used, such that the various phases run for the predetermined time unless completed earlier as measured by the humidity sensor 41 (and/or $H_2O_2$ sensor). In this regard, the controller 42 may also monitor the rate of change of the humidity level, during the evacuation phase, for example, and if the rate is slower than a threshold rate then the process may be stopped and the user prompted to replace the desiccant pod.

In some embodiments, the controller 42 may also turn the blower 47 on and off during the pulsed (noncontinuous) portion of the treatment phase. More particularly, it is generally desirable that the blower 47 is running any time disinfectant is being atomized in the air flow path, as this not only helps to circulate the atomized disinfectant to the enclosed chamber 31, but it also aids in the evaporation of the liquid disinfectant droplets as discussed above. However, the continuous air flow may in some enclosed chambers result in eddies or "dead zones" where less atomized disinfectant reaches. This may occur as a result of the particular geometry of the of the cabinet or enclosure being treated. Pulsing the air flow by cycling the blower 42 may advantageously help force more atomized disinfect into these dead zones to help ensure that proper disinfection occurs uniformly throughout the enclosed chamber 47. By way of example, the controller 42 may cause the blower 47 to cycle on and remain on while the disinfectant is being pulsed during the second portion of the treatment phase, but cycle off briefly between disinfectant pulses (noncontinuous operation).

As noted above, in some embodiments the separate fogger 35 (or fogging components, such as a compressor and atomizing nozzle) could be omitted. In a variation of the fogging injection station 32', the treatment fluid/disinfectant reservoir 36' may be connected directly to the evaporation chamber 48 without the air compressor 37' or atomizing nozzle 38', such that the disinfectant is evaporated directly into the air flow path without first being atomized. However, this may require a longer duration to bring the enclosed chamber 31' up to the desired level of disinfectant or humidity, and thus an extended treatment cycle.

A control panel 60 of the fogging injection station 32 illustratively includes a display 61 and indicators 62 (e.g., LEDs, etc.) as output devices, as well as user input devices 63 (e.g., buttons, touch screen, etc.) which are coupled to the controller 42 to allow a user to initiate and monitor the treatment cycle and the various operational phases (see FIG. 3). In some embodiments, the fogging injection station 32 may allow for calibration prior to a treatment cycle or as desired to calibrate the various sensors therein. During calibration, the fogging injection station 32 is not connected to an enclosure (a bypass tube may optionally be connected between the input and output ports 33, 34), and the blower 47 runs to cycle air through the fogging injection station. Calibration may be appropriate to remove humidity from the fogging injection station 32 from a previous treatment cycle, etc. The fogging injection station 32 may also allow for a forced extraction during a treatment cycle to provide forced desiccation through the desiccation chamber 45, essentially functioning as a dehumidifier to remove humidity from the enclosure 31.

Another example control panel configuration is a touch-screen display 160 shown in FIGS. 4-7. In the example shown in FIGS. 4-5, the controller 42 may advantageously store different types of enclosed chambers 31 and associated parameters/settings. This makes it easier and quicker for users to configure the fogging injection station 32 for use with different types of enclosed chambers 31. In the illustrated example, the user is first asked what type of enclosed chamber 31 is being disinfected, and two options are provided for selection (see FIG. 4), namely isolators and biological safety cabinets (although other types of enclosures may be listed in different embodiments). Once one of the types of enclosed chambers 31 is selected, then further information regarding the chamber may be collected by the controller 42 to determine the appropriate treatment cycle settings.

Figure 5:
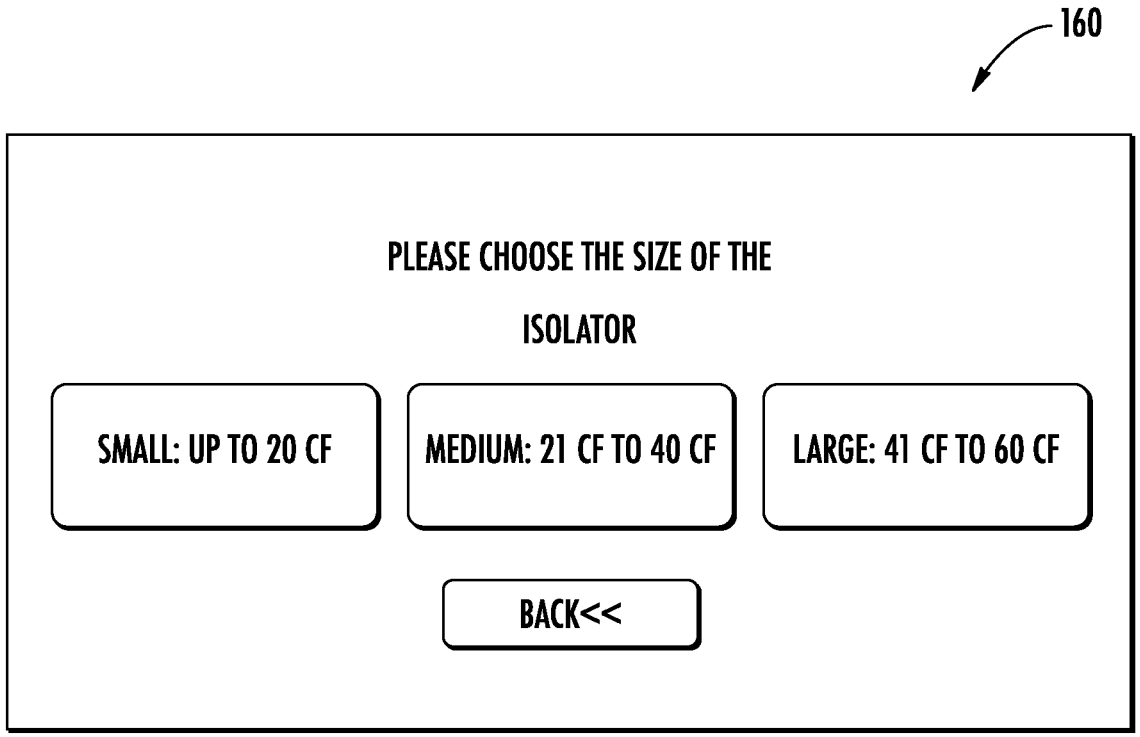

In the illustrated example, the user has chosen to treat an isolator, and the user is accordingly prompted to enter a size of the isolator (FIG. 5). Here, the user is presented with three options, namely small, medium, and large isolator sizes. However, other approaches may be used, such as allowing the user to enter dimensions of the isolator directly, or entering a make/model of the isolator from which the controller 42 may retrieve previously stored parameters (dimensions, volume, etc.) to select the appropriate treatment cycle settings. In some implementations, the controller 42 may store these settings locally, or interface with a database (e.g., via Wi-Fi, etc.) so that these settings may be stored and accessed across different fogging injection stations 32, for example.

Figure 6:
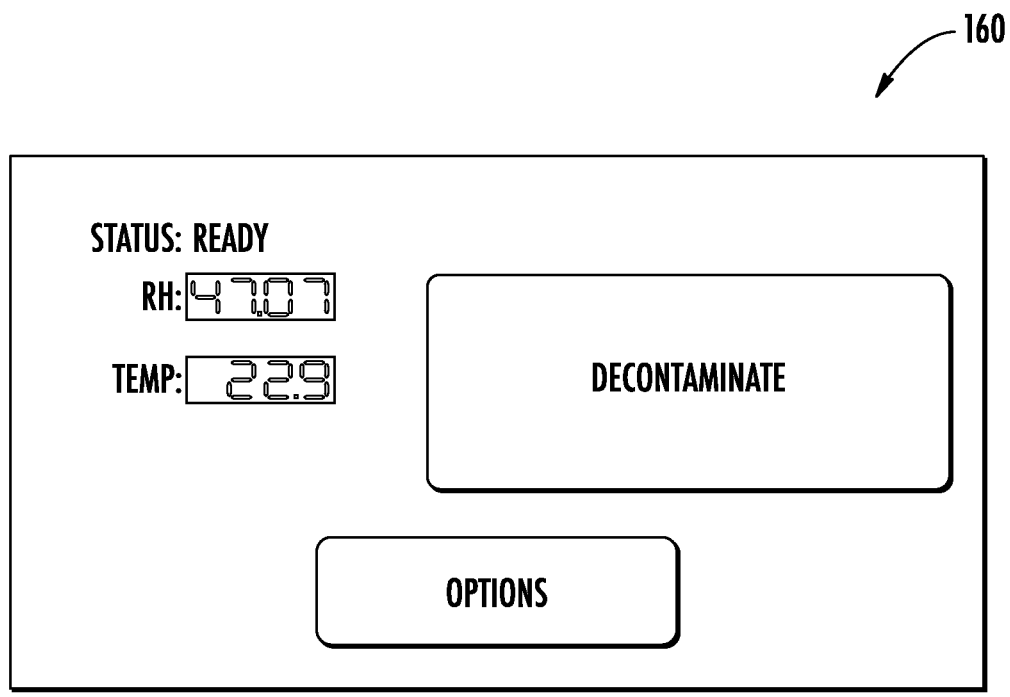
Figure 7:
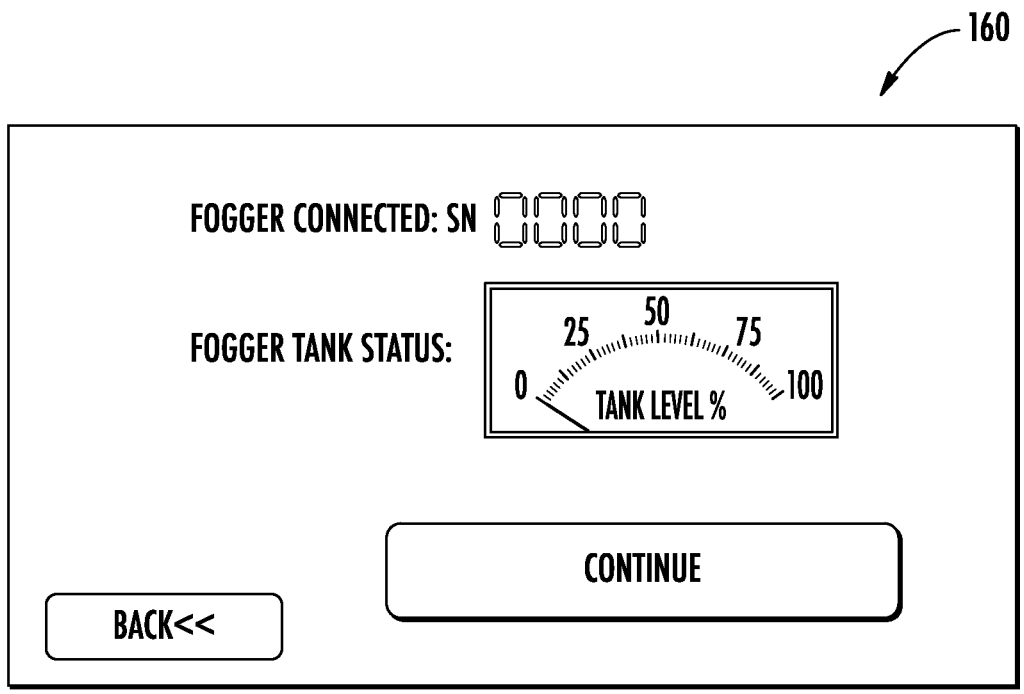

In the example of FIG. 6, current conditions are displayed, including the measured humidity and temperature of air within the airflow path. A "decontaminate" button allows for starting the treatment cycle, and an options button allows for the selection or customization of other treatment cycle settings and/or other settings of the fogging injection station 32 (e.g., Wi-Fi setup, display options, fogger pairing, etc.). Other status display settings may include a fogger tank status (e.g., disinfectant fill level) and paired fogger identification/status (see FIG. 7), although others may be provided as well.

Turning now to the flow diagram 90 of FIG. 9, a related method for disinfecting an enclosed chamber 31 illustratively begins at Block 91. Upon initiation of a treatment phase (Block 92), the controller 42 operates the air compressor 37 to introduce atomized disinfectant into the airflow path, as discussed further above (Block 93). When the treatment phase is complete (Block 94), the evacuation phase begins with ceasing operation of the air compressor 95 to stop the atomized disinfectant injection, at Block 95, along with operating the solenoid and airflow valve 43 to divert the airflow path through the dehumidification chamber 45 to remove atomized disinfectant from the airflow path, at Block 96, as also discussed above. Upon completion of the evacuation phase (Block 97), the method of FIG. 9 illustratively concludes at Block 98. However, in some embodiments, the optional neutralization phase may be performed along with additional evacuation/dehumidification as desired.

The fogging injection station 32 set forth herein advantageously provides desired efficacy, yet with a delivery platform that helps mitigate the risks to both staff and facilities, and may help decrease overall hazards involved with the decontamination process. Moreover, this approach also allows for the decontamination of self-contained germ-free enclosures like gnotobiotic, isolators, hypoxia and biological safety cabinets without the use of relatively high concentration level disinfectants (e.g., 50% and higher $H_2O_2$ solutions). Rather, the present approach may utilize relatively low-level concentrations, e.g., in the 7-10% range (or potentially less). Moreover, relatively low PPM levels (e.g., below 200 PPM) may be achieved without heating to provide safer operation and less potential for damage to the enclosures.

Many modifications and other embodiments will come to the mind of one skilled in the art having the benefit of the teachings presented in the foregoing descriptions and the associated drawings. Therefore, it is understood that the foregoing is not to be limited to the example embodiments, and that modifications and other embodiments are intended to be included within the scope of the appended claims.

The invention claimed is:

1. A system for disinfecting an enclosed chamber comprising:
- a housing;
- an inlet and an outlet carried by the housing to be connected in an airflow path with the enclosed chamber;
- a dehumidification chamber carried by the housing;
- a blower carried by the housing and connected to the airflow path between the inlet and outlet and configured to circulate air through the airflow path;
- an atomizing nozzle connected to a disinfectant fluid reservoir and an air compressor, the atomizing nozzle configured to atomize disinfectant within the airflow path during a treatment phase;
- an airflow valve connected in the airflow path between the inlet and dehumidification chamber; and
- a controller configured to operate the airflow valve to connect the dehumidification chamber into the airflow path during an evacuation phase, and disconnect the dehumidification chamber from the airflow path during the treatment phase.

2. The system of claim 1 further comprising a neutralizing fluid reservoir carried by the housing and a fluid valve connecting the neutralizing fluid reservoir to the airflow path between the inlet and outlet; and wherein the controller is further configured to, during a neutralization phase, operate the fluid valve to introduce neutralizing fluid into the airflow path.

3. The system of claim 1 wherein the controller is configured operate the air compressor continuously during a first portion of the treatment phase, and non-continuously during a second portion of the treatment phase.

4. The system of claim 1 wherein the dehumidification chamber comprises a desiccation chamber configured to receive a desiccation cartridge.

5. The system of claim 1 further comprising a humidity sensor connected in the airflow path between the inlet and outlet and to the controller, and wherein the controller is configured to operate the compressor during the treatment phase responsive to the humidity sensor.

6. The system of claim 5 wherein the humidity sensor comprises a hydrogen peroxide sensor.

7. The system of claim 1 wherein the blower is upstream from the atomizing nozzle in the airflow path.

8. The system of claim 1 wherein the controller is further configured to operate the blower non-continuously during the treatment phase.

9. The system of claim 1 further comprising an external disinfectant fluid port carried by the housing to be connected to the disinfectant fluid reservoir, and an external air compressor port carried by the housing to be connected to the air compressor.

10. A system for disinfecting an enclosed chamber comprising:
- a housing;
- an inlet and an outlet carried by the housing to be connected in an airflow path with the enclosed chamber;
- a desiccation chamber carried by the housing and configured to receive a desiccation cartridge;
- a blower carried by the housing and connected to the airflow path between the inlet and outlet and configured to circulate air through the airflow path;
- an atomizing nozzle connected to a disinfectant fluid reservoir and an air compressor, the atomizing nozzle configured to atomize disinfectant within the airflow path during a treatment phase;

an airflow valve connected in the airflow path between the inlet and desiccation chamber; and a controller configured to operate the airflow valve to connect the desiccation chamber into the airflow path during an evacuation phase, and disconnect the desiccation chamber from the airflow path during the treatment phase;

wherein the controller is configured operate the air compressor continuously during a first portion of the treatment phase, and non-continuously during a second portion of the treatment phase.

11. The system of claim 10 further comprising a humidity sensor connected in the airflow path between the inlet and outlet and to the controller, and wherein the controller is configured to operate the compressor during the treatment phase responsive to the humidity sensor.

12. The system of claim 10 wherein the blower is upstream from the atomizing nozzle in the airflow path.

13. The system of claim 10 wherein the controller is further configured to operate the blower non-continuously during the treatment phase.

14. The system of claim 10 further comprising an external disinfectant fluid port carried by the housing to be connected to the disinfectant fluid reservoir, and an external air compressor port carried by the housing to be connected to the air compressor.

15. A method for disinfecting an enclosed chamber comprising:

connecting an inlet and an outlet of a fogging injection station in a closed airflow path with the enclosed chamber, the fogging injection station comprising a housing, a dehumidification chamber carried by the housing, a blower carried by the housing and connected to the airflow path between the inlet and outlet and configured to circulate air through the airflow path, an atomizing nozzle connected to a disinfectant fluid reservoir and an air compressor and configured to atomize disinfectant within the airflow path during a treatment phase, an airflow valve connected in the airflow path between the inlet and dehumidification chamber, and a controller;

during an evacuation phase, using the controller to operate the airflow valve to connect the dehumidification chamber into the airflow path; and during the treatment phase, using the controller to operate the airflow valve to disconnect the dehumidification chamber from the airflow path.

16. The method of claim 15 further comprising using the controller to operate the air compressor continuously during a first portion of the treatment phase, and non-continuously during a second portion of the treatment phase.

17. The method of claim 15 wherein the dehumidification chamber comprises a desiccation chamber configured to receive a desiccation cartridge.

18. The method of claim 15 wherein the fogging injection station further comprises a humidity sensor connected in the airflow path between the inlet and outlet and to the controller, and further comprising using the controller to operate the compressor during the treatment phase responsive to the humidity sensor.

19. The method of claim 15 wherein the controller is further configured to operate the blower non-continuously during the treatment phase.

20. The method of claim 15 further comprising an external disinfectant fluid port carried by the housing to be connected to the disinfectant fluid reservoir, and an external air compressor port carried by the housing to be connected to the air compressor.

* * * * *